（12）United States Patent
Plechinger et al.

(10) Patent No.: US 7,108,785 B1
(45) Date of Patent: Sep. 19, 2006

(54) BLOOD CONDITIONING DEVICE

(75) Inventors: Hans Plechinger, Cranbrook (CA);
Hans-Jürgen Tiedtke, Aachen (DE);
Klaus Stevens, Lammersdorf (DE)

(73) Assignee: Convergenza Handelsanstalt, (LI)

( * ) Notice: Subject to any disclaimer, the term of this patent is extended or adjusted under 35 U.S.C. 154(b) by 0 days.

(21) Appl. No.: 10/012,634

(22) Filed: Nov. 6, 2001

Related U.S. Application Data

(60) Provisional application No. 60/246,200, filed on Nov. 6, 2000.

(51) Int. Cl.
*B01D 19/00* (2006.01)
*B01D 27/04* (2006.01)
*B01D 35/01* (2006.01)

(52) U.S. Cl. .................. 210/188; 210/194; 210/295; 210/435; 210/436; 210/512.1; 96/204; 96/205; 96/208; 95/261; 95/268; 95/269; 95/271

(58) Field of Classification Search ............... 210/188, 210/194, 295, 435, 436, 472, 512.1; 95/261, 95/268, 269, 271; 96/204, 206, 208
See application file for complete search history.

(56) References Cited

U.S. PATENT DOCUMENTS

| | | | | |
|---|---|---|---|---|
| 3,771,290 A | * | 11/1973 | Stethem | 210/304 |
| 4,344,777 A | * | 8/1982 | Siposs | 210/436 |
| 4,368,118 A | * | 1/1983 | Siposs | 210/136 |
| 4,662,906 A | * | 5/1987 | Matkovich et al. | 210/436 |
| 4,690,762 A | * | 9/1987 | Katsura | 210/436 |
| 4,932,987 A | * | 6/1990 | Molina | 210/436 |
| 5,630,946 A | * | 5/1997 | Hart et al. | 210/805 |
| 5,632,894 A | * | 5/1997 | White et al. | 210/436 |
| 5,744,047 A | * | 4/1998 | Gsell et al. | 210/767 |
| 5,849,065 A | * | 12/1998 | Wojke | 96/211 |
| 6,053,967 A | * | 4/2000 | Heilmann et al. | 96/208 |
| 6,398,955 B1 | * | 6/2002 | Fumiyama et al. | 210/304 |
| 6,478,962 B1 | * | 11/2002 | Brockhoff et al. | 210/512.1 |
| 6,517,732 B1 | * | 2/2003 | Brockhoff et al. | 210/782 |
| 6,827,862 B1 | * | 12/2004 | Brockhoff et al. | 210/787 |

FOREIGN PATENT DOCUMENTS

| DE | 19719555 A1 | * | 11/1998 |
|---|---|---|---|
| GB | 2063108 | * | 6/1981 |

* cited by examiner

*Primary Examiner*—Krishnan S. Menon
(74) *Attorney, Agent, or Firm*—Beck & Tysver, P.L.L.C.

(57) ABSTRACT

A blood conditioning device having a housing with a helical blood acceleration section which includes a helical flow path for impressing centrifugal forces on the entrained bubbles in the blood to concentrate them towards the center of the flow path, a bubble pick off tube aligned with the centerline of the acceleration section which collects and recirculates the bubbles to the cardiotomy reservoir upstream of the device during operation, and a blood filtration section to intercept the flow of particles in the blood.

3 Claims, 7 Drawing Sheets

BLOOD CONDITIONING DEVICE

This application claims priority to the provisional application 60/246,200 filed Nov. 6, 2000

FIELD OF THE INVENTION

The present invention relates generally to the extracorporeal circulation of blood during open heart surgery, and more particularly to a device for conditioning blood prior to returning the blood to the patient.

BACKGROUND OF THE INVENTION

Open heart surgery is performed on a "still" heart. The patient's blood is circulated by an extracorporeal system, which includes a blood pump, a cardiotomy reservoir and an oxygenator. In operation, blood is drawn from the patient and pumped through the oxygenator and then returned to the patient. In many instances blood is scavenged from the surgical site and this recovered blood is added to the system through the cardiotomy reservoir. As a consequence, surgical debris and air bubbles may be introduced into the system at this point and it is important that the particulate debris and bubbles not be administered to the patient.

It is the conventional standard of care to place a so-called "arterial filter" in the blood line to intercept and capture particles and gas bubbles before the blood is returned to the patient's body. Filters of this type capture both gas bubbles and particles on a filter mesh. However conventional arterial filters are problematic. Typically the volume of an atrial filter is large to maximize the ability of the device to collect and hold gas bubbles. Captured bubbles are retained on the mesh during the entire surgical procedure. Each bubble that is retained reduces the filter mesh surface area available for particulate collection. It is possible that a large particle load will increase the pressure drop across the filter. This "clogging" effect can increase the pressure on the captured bubbles and force them though the filter. As a consequence of this problem the size of the physical membrane of the arterial filter is very large to provide a margin of safety. However this increases the surface area in contact with blood which is undesirable and increases priming volume which is undesirable. It should also be noted that the mesh size of a typical filter is inadequate to capture small bubbles. Consequently the conventional arterial filter is not efficient at handling bubbles and it is improperly sized for the typical particulate load.

It must also be noted that blood is a very delicate organ and surface contact, turbulence and pressure drops within the system can injure the blood. These properties of blood must be accommodated as well.

SUMMARY

In the present invention the blood conditioning device has two main connections. There is a blood input port and a blood output port. A third connection is used to purge or prime the device. In some embodiments of the device this line is always open and is used for continuous recirculation of blood containing bubble to the cardiotomy reservoir.

The blood conditioning device relies on a first dynamic stage to remove bubbles from the mixed flow of bubbles and particles in blood.

The dynamic stage passes the bubble free but particle laden blood flow to a second mechanical filter media stage where the particles are trapped. The gas bubbles maybe collected and retained in the device or returned with a modest blood flow to the cardiotomy reservoir through the third purge or recirculation connection.

The blood conditioning device is disposable and used once. The particulate debris is retained in the device and discarded at the conclusion of the procedure.

In the first dynamic stage, the blood is delivered to a blood centrifuge section, which imparts a strong radial acceleration to the blood flow. The pressure gradient is created by forcing the blood along a helical flow path. The radial acceleration causes bubbles both large and small to migrate toward the center streamline of the flow. A bubble pick up may be placed in the zone where the bubbles accumulate. The bubble pick up collects the bubbles and it is connected to the cardiotomy reservoir to extract the bubbles from the device. In an alternate embodiment of the device there is no extraction tube or bubble pick off tube and the bubbles are allowed to coalesces and accumulate in the device during operation. This dynamic stage is referred to as the "helix" in the description.

To purge or prime the device a momentary operation valve is placed on top of the device. The preferred versions of this valve opens side holes in the bubble pick up tube in order to release gross air from the device to the cardiotomy reservoir.

BRIEF DESCRIPTION OF THE DRAWINGS

Throughout the several figures of the drawing identical reference numerals indicate identical structure, wherein.

DETAILED DESCRIPTION

Figure 1:
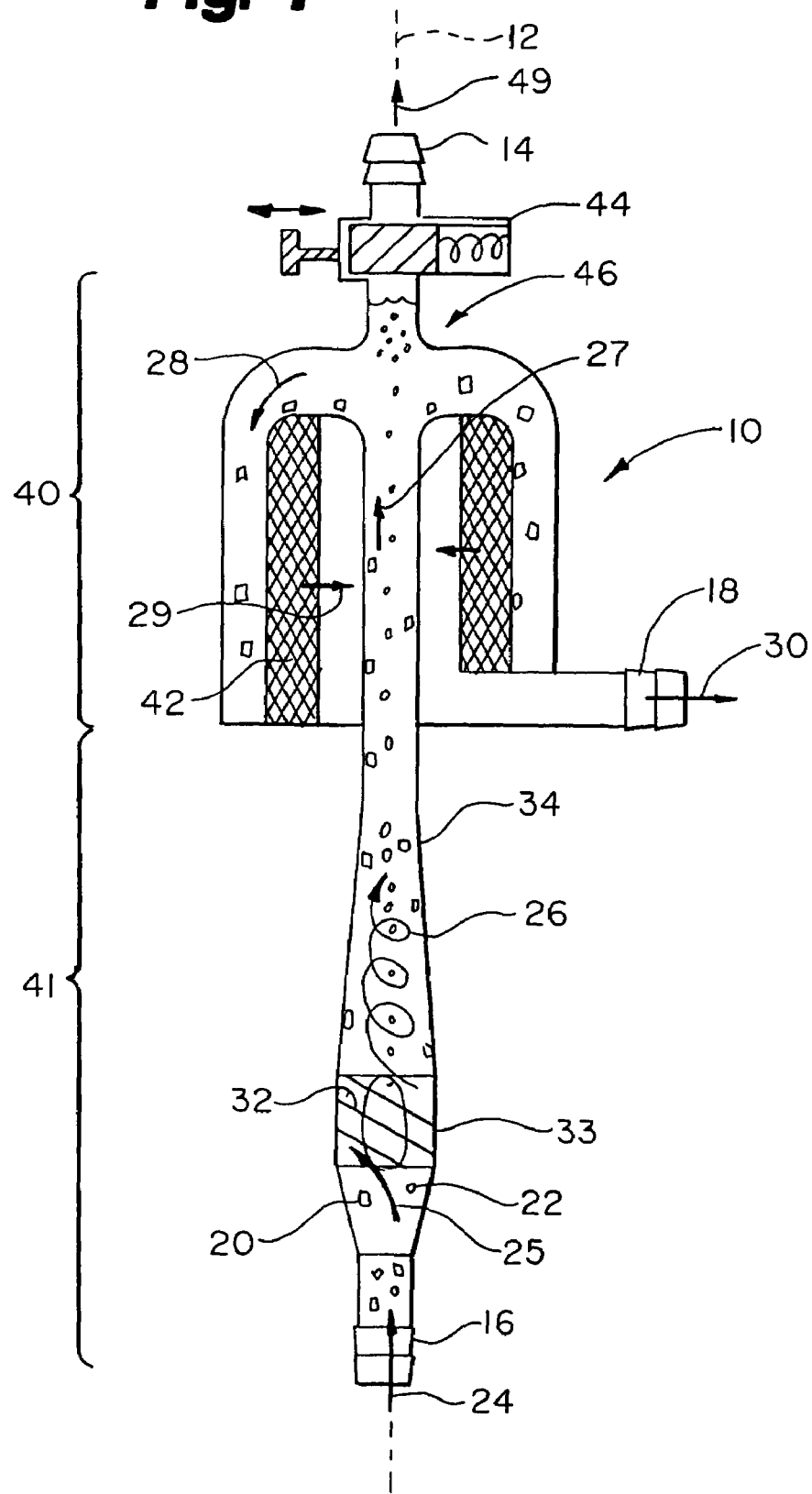
FIG. 1 is a schematic cross section of a first embodiment of the device.

FIG. 1 shows a first embodiment of the blood conditioning device 10. This representative device is shown in a schematic cross section and it is generally symmetric about axis 12. In use this device is mounted vertically with the purge/recirculation port 14 located at the "top". Although the device can be used for conditioning blood in any perfusion circuit it is preferred to couple the input port 16 to the source of blood and to connect the output port 18 directly to the cannula used to deliver blood to the patient. The blood pump supplies the modest pressure difference required to operate the device. The oxygenator and cardiotomy reservoir are of conventional design and they are used in the conventional fashion.

In the various figures the small squares typified by square 20 represent surgical debris with a density slightly greater than blood. The small circles typified by circle 22 represent bubbles or micro bubbles in the blood flow 24. The bubbles have a size of approximately 40 microns or more and micro-bubbles have a diameter of 40 microns or less. At the inlet port 16, the blood flow 24 has a uniform distribution of particles and bubbles in the input stream, and is called a "mixed blood flow" herein. The mixed blood flow 25 enters an acceleration chamber or "helix" 33" of the dynamic section 41. One or more blades 32 form a helical flow path in the acceleration chamber 33. The blood flow, which leaves the helix 33, has a spiral motion as indicated by blood flow arrow 26. The radial acceleration is strong enough to cause the bubbles to accumulate along the centerline or axis 12 of the device 10. The length of the discharge tube 34 is sufficiently long to permit nearly complete separation of the bubbles from the particles. In this first embodiment of the device these bubbles coalesce and migrate toward zone 46.

Eventually the spiral motion of the blood flow is reduced as indicated by blood flow 27 and the bubble free blood flow 28, leaves the dynamic section 41 and turns to enter the mechanical separation section 40.

The blood now free of bubbles enters a flow path that intercepts a membrane 42. The annular membrane 42 filters the blood flow and the particles adheres to the surface of the membrane while the blood passes through the membrane as depicted by blood flow 29. The blood accumulated behind the membrane 42 is delivered to the output port 18 and the now conditioned blood flow 30 is introduced into the patient.

In operation the particles and blood turn into the mechanical separation section 40 while the buoyancy of the bubbles causes them to coalesce into larger bubble and form a bubble rich volume or zone 46 trapped near the stopcock 44. The purge stopcock 44 may be used to prime the device during setup and may be used to periodically return the bubble rich accumulated volume 46 to the blood cardiotomy reservoir during operation.

Figure 2:
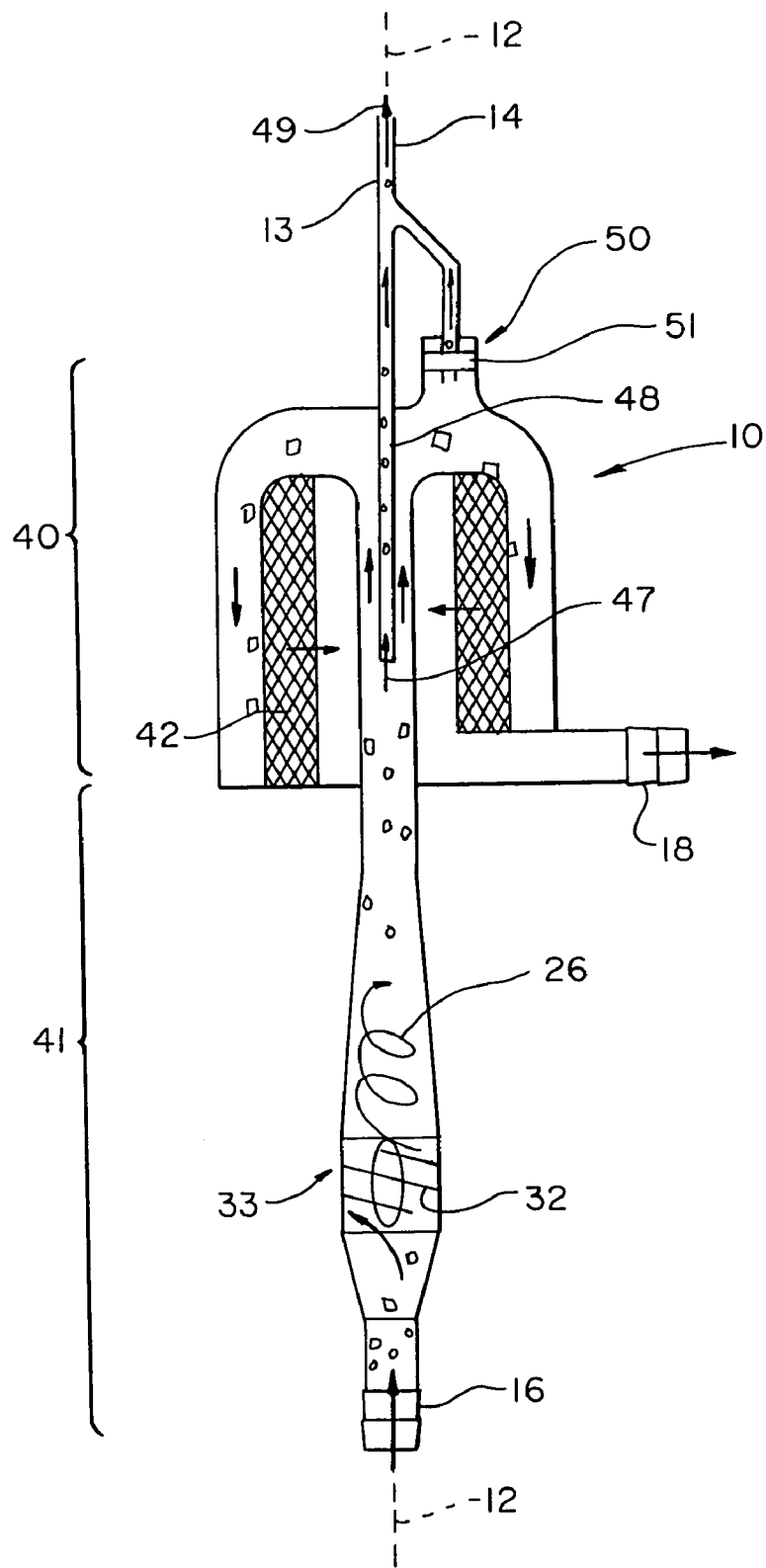
FIG. 2 is a schematic cross section of a second embodiment of the device.

FIG. 2 is a schematic cross section of a second embodiment of the blood conditioning device 10. In this second embodiment a bubble pick off tube 48 is positioned to intercept the stream of micro-bubbles from the dynamic section 41. The opening 47 of the bubble pick off tube 48 is sized to capture the blood flow near the centerline 12 of the dynamic section. The opening 47 establishes a small regulated blood flow 49 from the device to the cardiotomy reservoir (not shown) which carries the bubbles back to the cardiotomy reservoir. This recirculation line 13 is always open.

Figure 3:
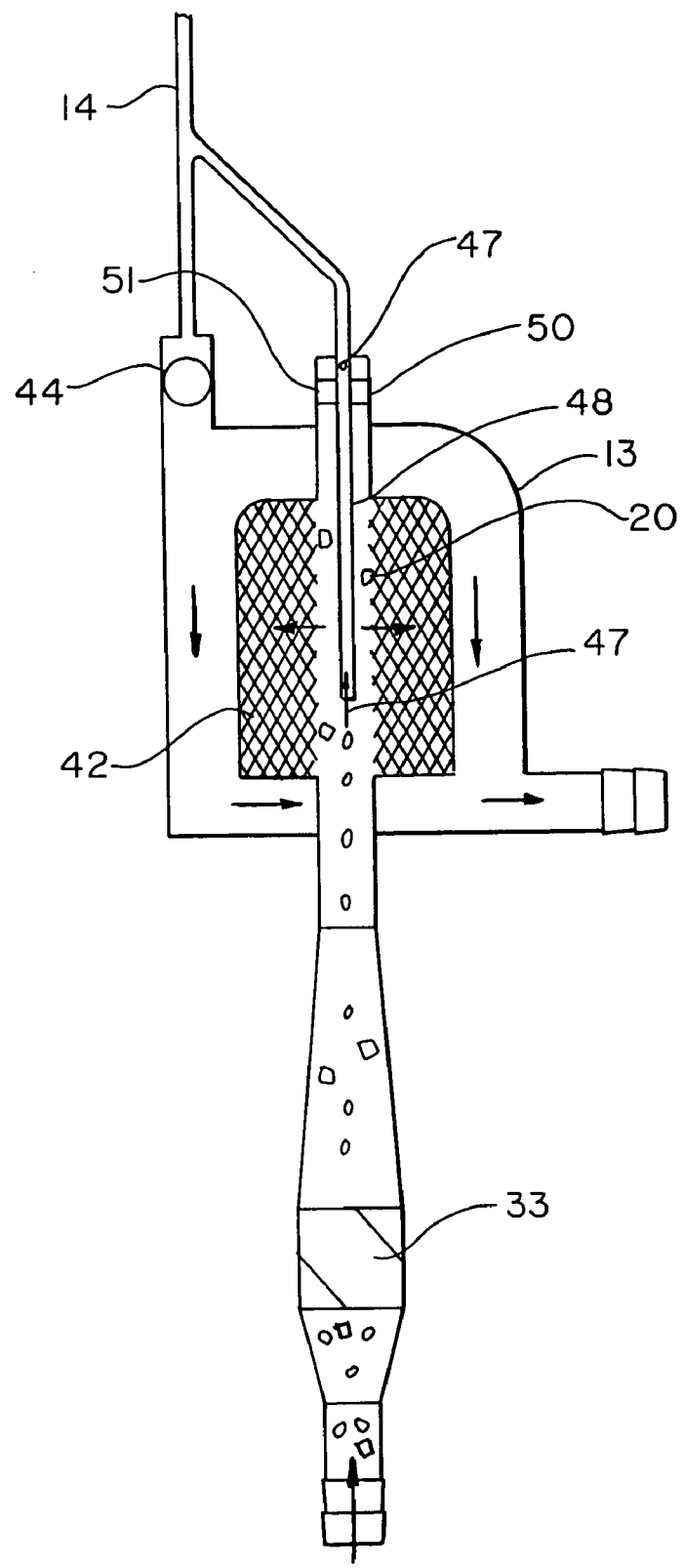
FIG. 3 is a schematic cross section of a third embodiment of the device.

FIG. 3 is an alternate embodiment incorporating a bubble pick off 48 which pulls bubbles from the device through opening 47. In this device operates similar to FIG. 2 but in contrast the particles can directly engage the filter mesh 42 as the blood flow flows in an outward direction from the center of the device.

FIG. 3 also shows the preferred form of momentary operation valve 50. The momentary operation valve 50 is provided at the top of the housing to allow the user to purge or prime the device. When "open" the valve 50 allows the gross air from the interior volume of the device to be purged into the cardiotomy reservoir. When closed the interior volume of the device is closed off but the bubble pick off tube remains open to the cardiotomy reservoir.

Figure 7A:
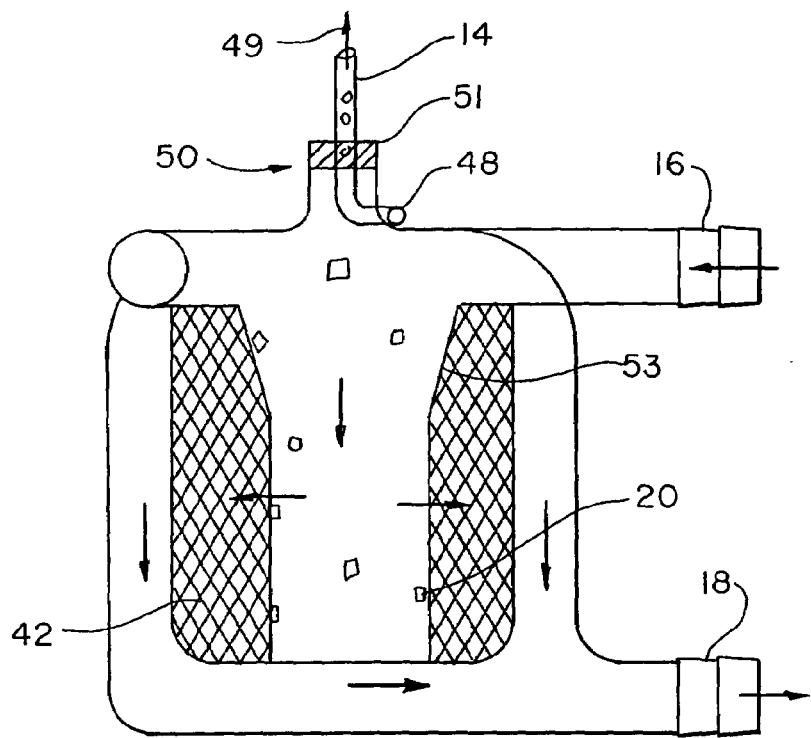
FIG. 7A is a schematic cross section of a seventh embodiment of the device; and, FIG. 7B is a schematic cross section of a seventh embodiment of the device.

The preferred form of the valve includes a ring 51 which can slide between two positions. In the first position the ring covers side holes 47 in the bubble pick up tube 48 and is in the "closed" position. The valve 50 in FIG. 7A is shown in this state. In the second "open" position the ring 51 uncovers the side holes 47 in the bubble pick off tube 48 as seen in the FIG. 3 among others. In the "open" position the interior volume of the housing 13 is open to the reservoir.

This valve may be operated to bleed the system both prior to use and during a surgery. In general the valve 50 is closed and remains open only while operated by the perfusionist.

Figure 4:
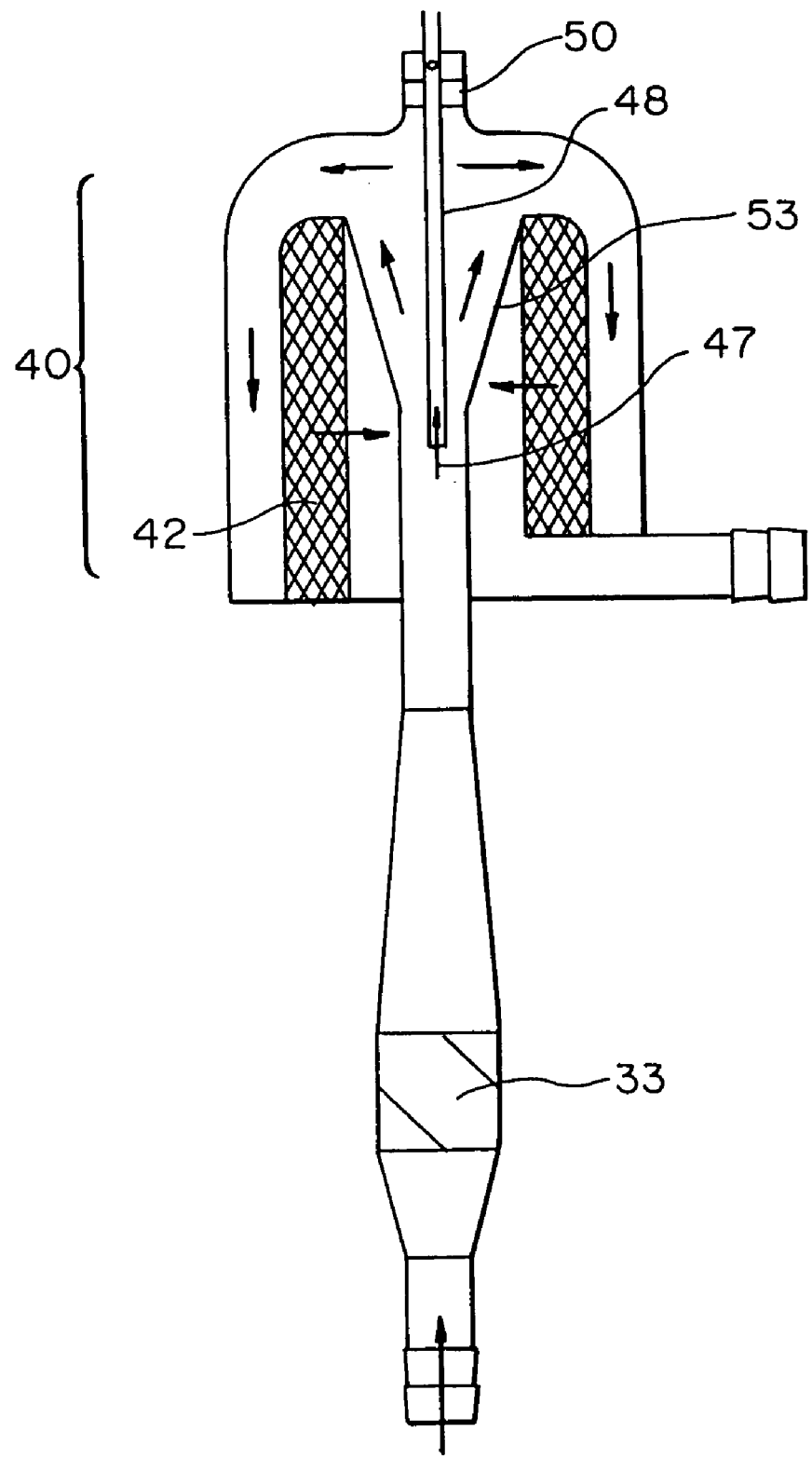
FIG. 4 is a schematic cross section of a fourth embodiment of the device.

FIG. 4 is an alternate embodiment of the invention which includes a diverging channel 53 to decrease the velocity of the blood flow after the bubbles have been picked off at opening 47. It is expected to be advantageous to decrease the velocity in the mechanical filtration section 40.

Figure 5:
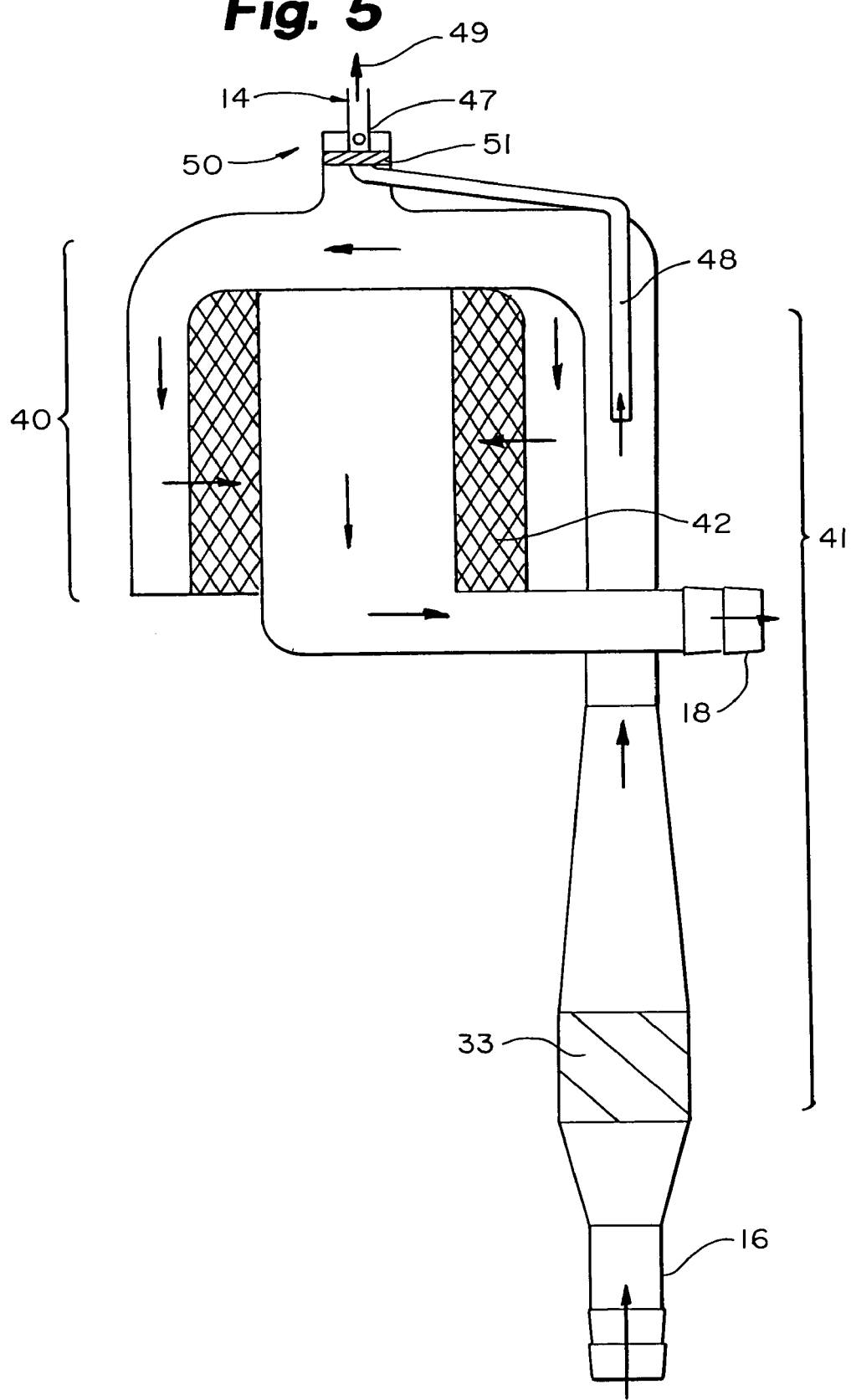
FIG. 5 is a schematic cross section of a fifth embodiment of the device.

FIG. 5 is an alternate embodiment of the device having a "side by side" configuration the dynamic section 41 located substantially next tot he mechanical filtration section 40. The principle advantage of this configuration is the ability to see the bubble pick off 48 and related area of the dynamic section during operation and provides more options for flow dynamic optimization in the two sections.

Figure 6A:
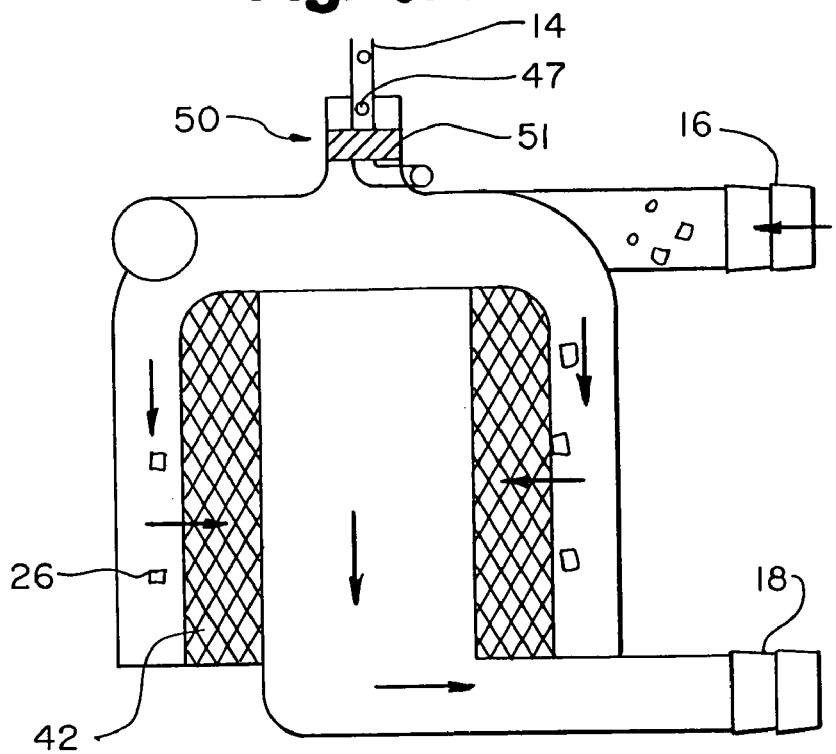
FIG. 6A is a schematic cross section of a sixth embodiment of the device.

FIG. 6A is side elevation of an alternate embodiment of the device. In this configuration the device is very compact. In this version of the device the particles 20 are captured on the outer surface of the annular filter mesh 42. while the bubbles pass the helix 33 in advance and are picked up in line 48. On top of the device the preferred momentary operation valve 50 is schematically shown, opening side hole to the recirculation line to release gross air upon operation.

Figure 6B:
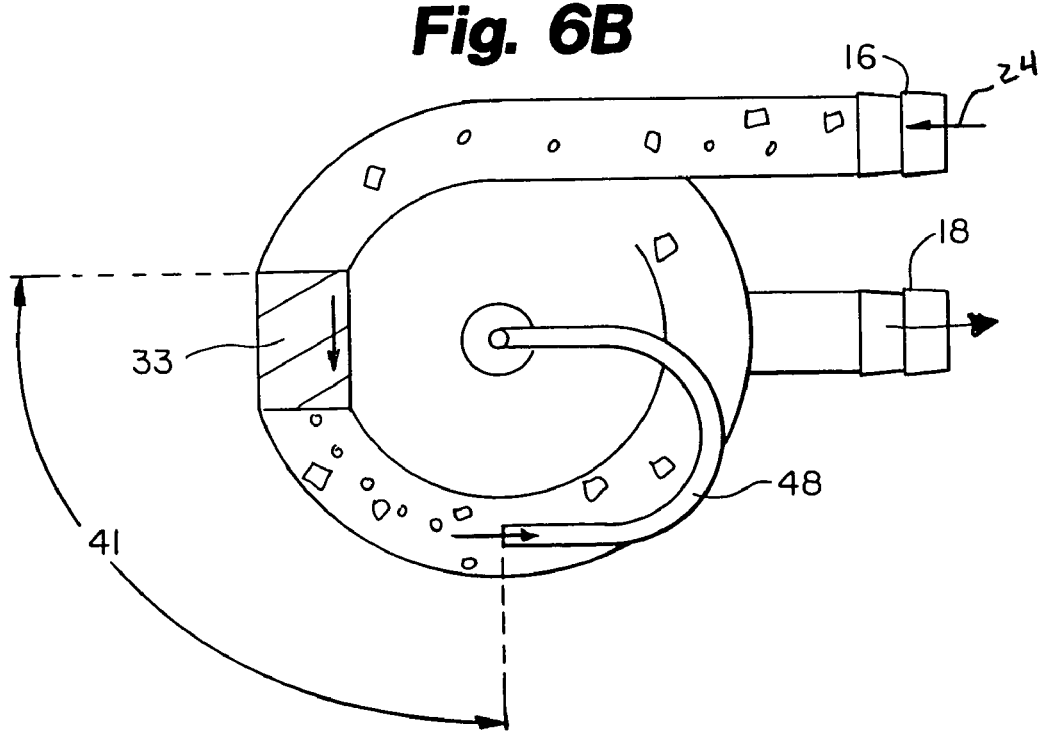
FIG. 6B is a schematic cross section of a sixth embodiment of the device.

FIG. 6B is top view of an alternate embodiment of the device. In this view one can see that the helix 33 is located in a circular flow path. In general the input mixed blood flow 24 turns through about 90 degrees before it enters the helix 33.

The dynamic section 41 extends around the circle and the bubble pick off 48 is downstream through another 90 degrees of turning.

FIG. 7A is side elevation of an alternate embodiment of the device. In this embodiment in contrast to FIG. 6 the blood flow carrying particulates is from the interior of the device to the exterior as typified by the location of particle 20. In this embossment conical surface or funnel is used to accelerate blood flow as it enters the filter zone.

Figure 7B:
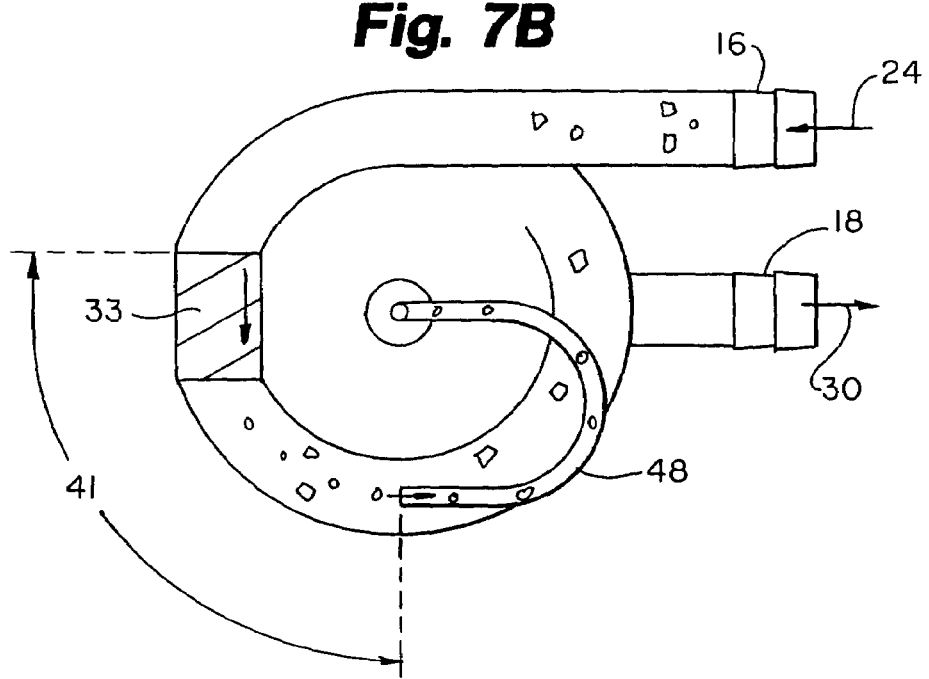

FIG. 7B is top view of an alternate embodiment of the device. In this version of the device the helix 33 is located part way round the circumference of the device with a bubble pick off 48 located downstream of the helix 33.

What is claimed is:

1. A blood conditioning device comprising:
   a housing having a first blood inlet port, a second blood outlet port and a third purge/recirculation port;
   a helical blood acceleration section coupled to said first blood inlet port for removing bubbles entrained in blood from the blood entering the inlet, and producing an acceleration section output flow;
   a mechanical filtration section coupled to said helical blood acceleration section, receiving said acceleration section output flow and for trapping particles carried by said flow producing a device output flow for a patient wherein the blood acceleration section includes a helical flow path and a bubble pick off tube placed to remove bubbles entrained in blood; said bubble pick off tube coupled to the third purge/circulation port and having a continuous recirculation flow during operation of the device.

2. A blood conditioning device for removing bubbles and particles from a stream containing a mixed flow having both particles and bubbles, said device comprising:
   a first dynamic separation section for separating bubbles entrained in blood from said mixed flow, generating a flow of particles and blood but free of bubbles, said dynamic section being a helical blood acceleration section for impressing centrifugal forces on the bubbles, and an extended separation path for allowing bubbles entrained in blood to collect on the centerline of said extended separation path;

a purge/recirculation port having continuous recirculation flow in communication with said centerline of said first dynamic separation section and through which bubbles entrained in blood are drawn out of the dynamic separation section, flowing in the same direction as the mixed flow and of the flow of particles and blood through the dynamic separation section; and a second section coupled to said first section having a filter membrane arranged to intercept the flow of particles and blood generating a flow of blood free of both particles and bubbles.

3. A blood conditioning device according to claim 2, further comprising a cardiotomy reservoir upstream of the first dynamic section and wherein said purge-recirculation port is in communication with said cardiotomy reservoir, such that bubbles entrained in blood that are drawn off through the purge/recirculation port are directed into the cardiotomy reservoir.

* * * * *